(12) United States Patent
Bartulovic et al.

(10) Patent No.: US 6,177,682 B1
(45) Date of Patent: Jan. 23, 2001

(54) INSPECTION OF BALL GRID ARRAYS (BGA) BY USING SHADOW IMAGES OF THE SOLDER BALLS

(75) Inventors: Vuk Bartulovic, Beaconsfield; Miljenko Lucic, Lachine; Gabriele Zacek, Montreal, all of (CA)

(73) Assignee: Novacam Tyechnologies Inc., Montreal (CA)

(*) Notice: Under 35 U.S.C. 154(b), the term of this patent shall be extended for 0 days.

(21) Appl. No.: 09/176,249

(22) Filed: Oct. 21, 1998

(51) Int. Cl.[7] ................................................ G01N 21/56
(52) U.S. Cl. ................................ 250/559.44; 250/559.12; 356/237.4; 382/150
(58) Field of Search ........................ 250/559.44, 559.22, 250/559.4, 559.19, 559.12, 559.29, 559.3, 208.1; 356/237.4, 237.5, 376; 382/150, 149, 151; 257/738, 779, 780

(56) References Cited

U.S. PATENT DOCUMENTS

| | | | |
|---|---|---|---|
| 5,465,152 | 11/1995 | Bilodeau et al. | 356/371 |
| 5,574,801 | * 11/1996 | Beillon | 382/150 |
| 5,621,530 | 4/1997 | Marrable, Jr. | 356/394 |

\* cited by examiner

Primary Examiner—Que T. Le
(74) Attorney, Agent, or Firm—James Anglehart; Swabey Ogilvy Renault

(57) ABSTRACT

A method for measuring such parameters as height, position, shape, colinearity, and coplanarity of arrays of minute objects on the surface of integrated circuits, such as Ball Grid Arrays (BGA), all in one simple and straight forward procedure during the manufacturing process of integrated circuits. Shadows of the objects are created on the substrate through the use of x-rays or other light sources placed at predetermined distances and angles from the objects. An imaging device obtains images from the shadows cast onto the substrate and the images are then analyzed to determine if they meet predefined parameters. Multiple sources of illumination can be used to illuminate the array in order to create a more precise image for analysis and three dimensional images of the BGA can be created for analysis.

25 Claims, 7 Drawing Sheets

FIG_2

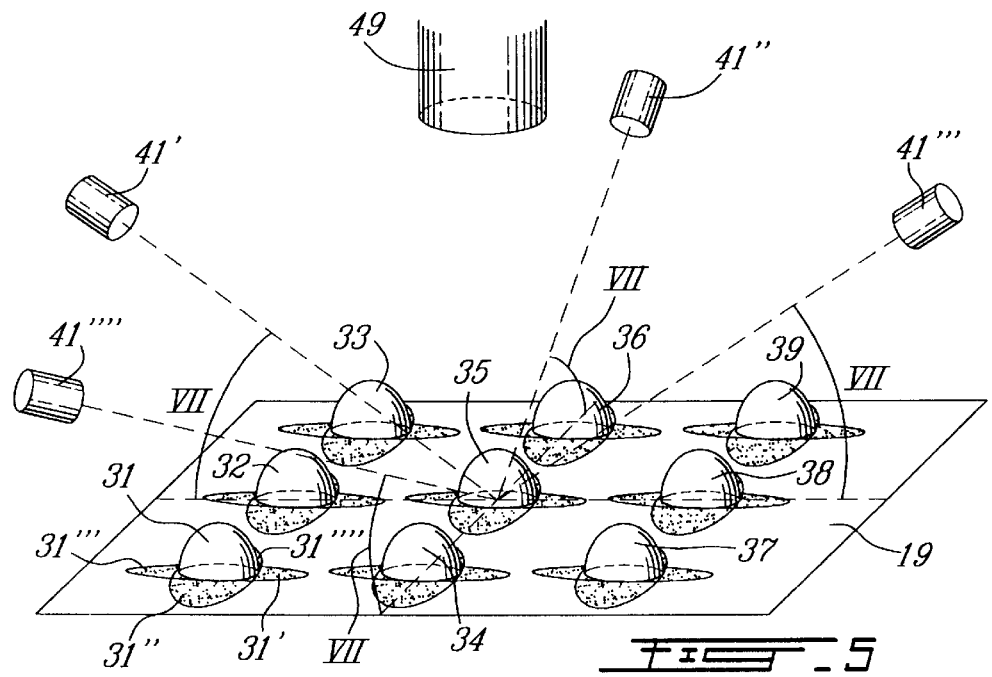
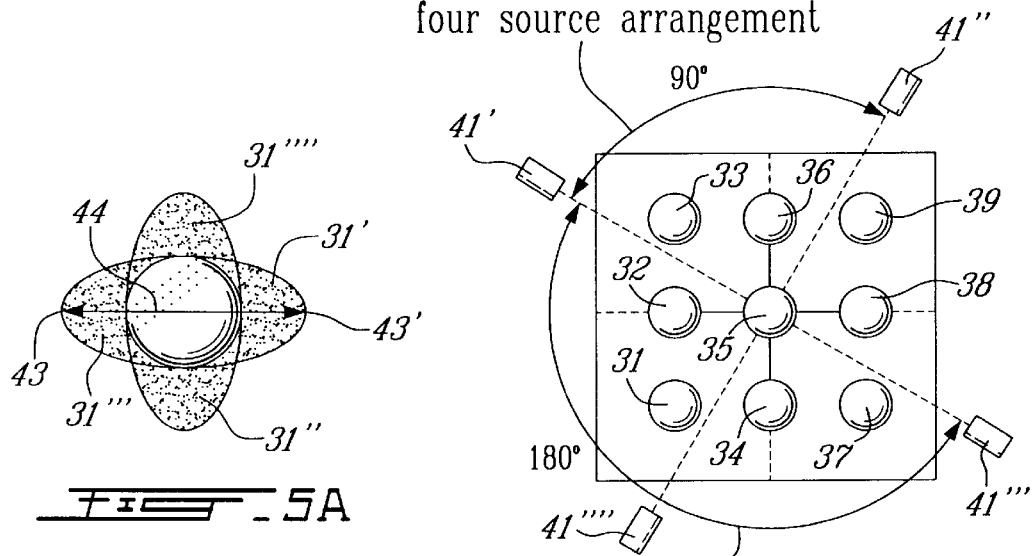

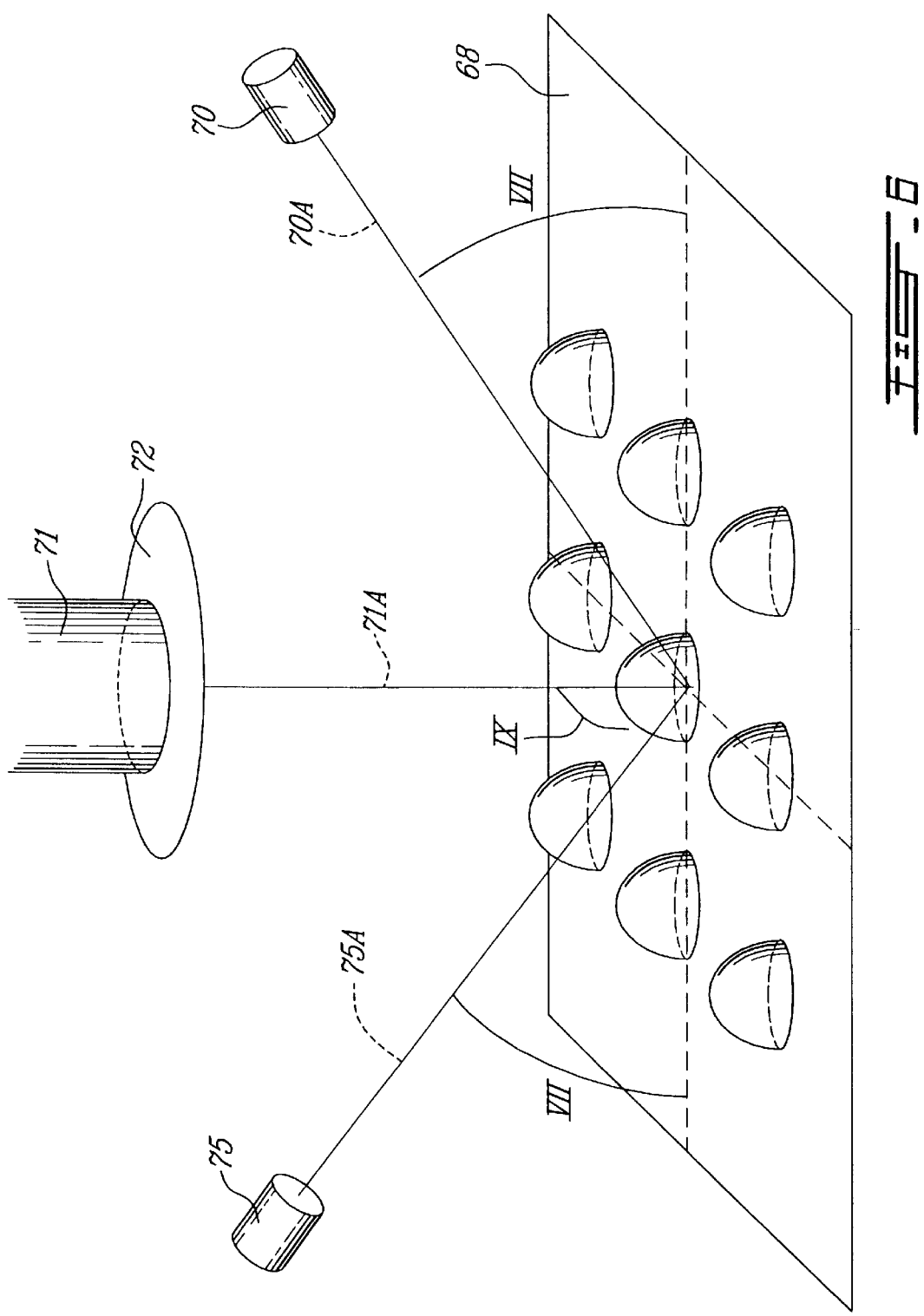

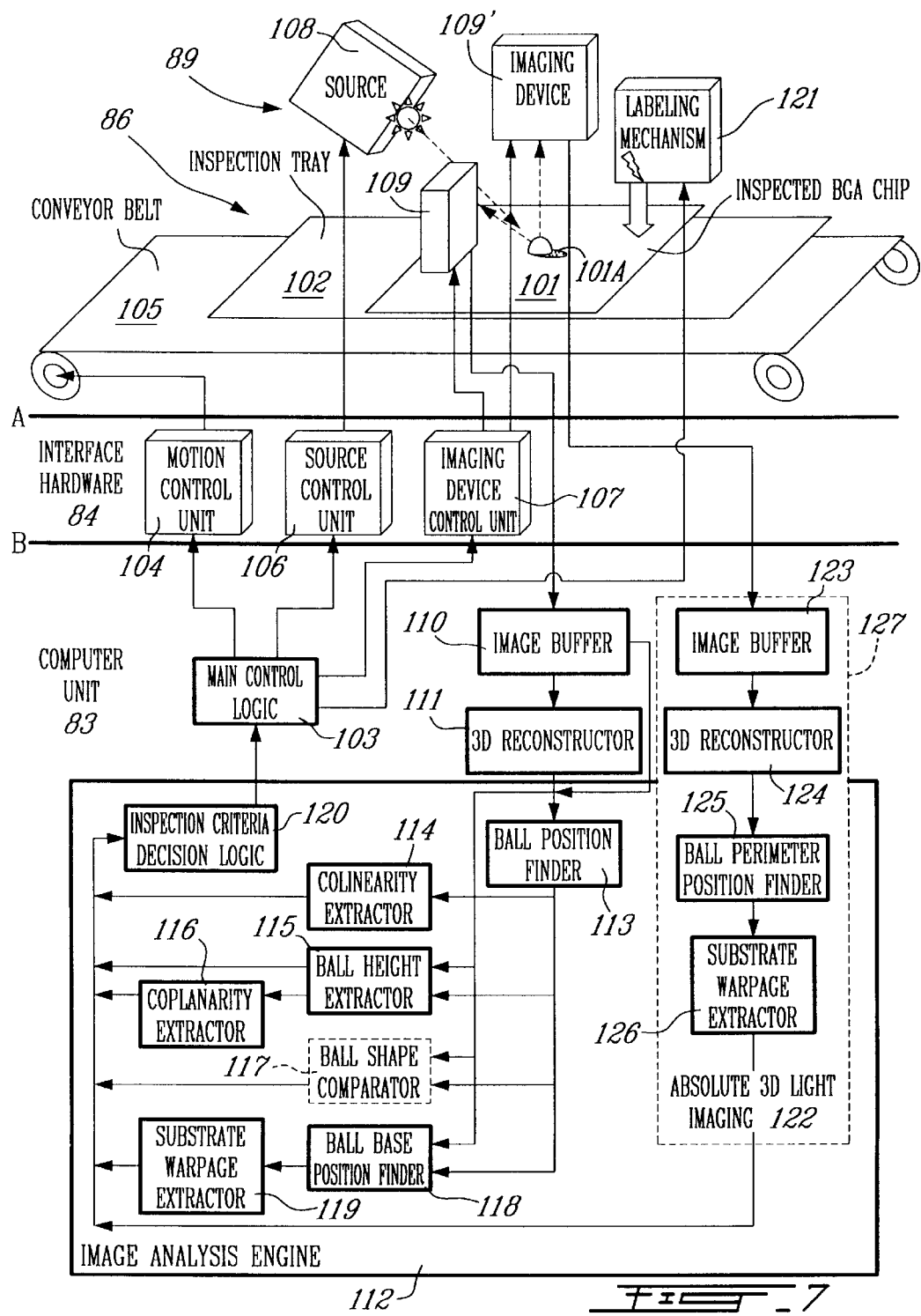

INSPECTION OF BALL GRID ARRAYS (BGA) BY USING SHADOW IMAGES OF THE SOLDER BALLS

FIELD OF THE INVENTION

The present invention relates to the inspection of solder balls in a ball grid array (BGA) on an integrated circuit chip package or similar structure. More particularly it relates to a method and apparatus for the inspection of the BGA to determine if the components of the BGA or similar structure meet certain predefined parameters.

BACKGROUND OF THE INVENTION

The inspection of packaging of electronic devices such as integrated chip (IC) packaging is well known in the art and is widely used in the electronic industry. ICs, electronic chip or chip packages, in this case of BGA types, are passed in a tray through the inspecting device. The purpose of the inspection is to measure the coplanarity (relative heights), colinearity (alignment) and the height of each individual ball of the solder balls on the BGA of an IC chip. As is known in the prior art these height measurements can be accomplished with laser triangulation methods, interferometry, and other non-contact measurements. However all tend to be complex and difficult to implement in a manufacturing setting.

A number of methods also exist wherein some part of the measuring device touches a portion of the BGA as exemplified by U.S. Pat. No. 5,621,530: "Apparatus and Method for Verifying the Coplanarity of a Ball Grid Array", issued Apr. 15, 1997. That patent describes an apparatus and method that places the IC with a BGA in the so-called live bug mode (i.e. the BGA is facing down) on a transparent surface and directs light through a series of mirrors onto the BGA. The reflected image is then analyzed to determine if the tips of all of the solder balls rest on the transparent surface. The focus information is then used to determine the distance to each solder ball which provides an indication of the coplanarity of the solder balls of the BGA. U.S. Pat. No. 5,465,152: "Method for Coplanarity Inspection of Package or Substrate Warpage for Ball Grid Arrays, Column Arrays and Similar Structures", issued Nov. 7, 1995, provides another apparatus and method for determining coplanarity and warpage. This invention uses index pads which are positioned on the substrate of the BGA. The pads reflect specific incident radiation from which the alignment and heights of the solder ball tops with respect to the surrounding array can be determined. The invention, from the information so obtained, allows one to determine the degree of coplanarity or substrate warpage.

However, the current methods tend to be limited in the parameters each can verify and check. The current methods like the ones described in the two patents mentioned above, for the most part use triangulation methods and specialize in the inspection of one or two parameters (e.g. coplanarity in the examples noted above). Thus, what is needed is a non-invasive easily implemented system which can measure and verify a wide variety of parameters in an expeditious manner. A system which would be able to measure such parameters as height, position, shape, colinearity, and coplanarity all in one simple and straight forward process during the manufacturing process. A method which allows a full three dimensional (3-D) inspection of the chip quality during the manufacturing process.

SUMMARY OF THE INVENTION

Among the goals of the present invention are the providing of a non-invasive easily implemented system which can measure and verify a wide variety of parameters of a solder ball grid array on an integrated circuit chip in an expeditious manner. A method which has a much wider scope than current methods which allows the full 3-D inspection of the chips quality during the manufacturing process.

In brief, the invention achieves these goals by using one or more X-ray or light sources to create shadows of the solder balls of a ball grid array on the substrate on which the BGA is located, then to image the BGA with the shadows cast by the balls of the array and then analyze the images so obtained to determine if they meet predefined parameters.

According to the invention there is provided a system for verifying that a ball grid array on an integrated circuit conforms to specific position parameters. This system includes a source of electromagnetic radiation which projects that radiation at a predetermined angle onto a substrate of the integrated circuit on which substrate surface is said array, an imaging device to obtain an image or images of shadows cast by the minute objects and means to analyze said image to obtain contour data of the shadows cast. In an additional aspect of the invention, it provides the ability to analyze the contour data to determine if the balls meet certain predefined parameters.

In yet another aspect of this invention, the radiation used to illuminate the solder balls of the BGA can either be x-rays or light. Generally, if x-rays, the x-ray source and the imaging device are positioned on opposite sides of the chip being imaged. If light, the light source and imaging device are positioned on the same side of the chip being imaged.

In yet another aspect of this invention, in the preferred embodiment, the predetermined angle at which the axis of illumination of the radiation projected at the BGA strikes the substrate can vary from 10 to 40 degrees. Additionally, in the preferred embodiment, a projection onto the substrate of the path of the axis of illumination of the radiation used to illuminate the BGA can be any angle of from 5 to 40 degrees with the primary orthogonal axis of the BGA.

In one variation of the invention, multiple sources of illumination are provided to illuminate the BGA at the same predetermined angle but from different directions. Generally, the number of sources are two or four in the preferred embodiment of this variation and the sources are positioned at equidistant angles from each other. Thus, by using multiple sources of illumination a more precise image is obtained for analysis and the option exists to create a three dimensional image of the BGA for analysis.

In yet another variation of the invention multiple imaging devices are used, generally two or three imaging devices in the preferred embodiment of this variation. Using the multiple images obtained, the system can preform sophisticated analysis on the BGA and produce a three dimensional image of the BGA for analysis.

The invention also provides a method for verifying that an array of minute objects on a workpiece conform to specific parameters. The method includes: projecting electromagnetic radiation at a predetermined angle onto a substrate surface of the workpiece on which substrate surface are positioned an array of minute objects, imaging the shadows cast by the minute objects as a result of being illuminated by the electromagnetic radiation, and analyzing the images so obtained to determine if the array of minute objects on the substrate meet certain predefined parameters.

BRIEF DESCRIPTION OF THE DRAWINGS

The invention will be better understood by an examination of the following description, together with the accompanying drawings, in which:

FIG. 5 depicts schematically a subsection of an illuminated BGA in another version of the preferred embodiment which uses multiple sources of illumination;

FIG. 5A provides an overhead view of one of the illuminated solder balls of FIG. 5;

FIG. 5B provides on overhead view of one variation of the invention using multiple sources of illumination;

FIG. 6 depicts schematically a subsection of an illuminated BGA in another version of the preferred embodiment which uses multiple imaging devices; and FIG. 7 provides a block diagram of the overall system and its implementation with some variations.

DETAILED DESCRIPTION OF THE PREFERRED EMBODIMENT

Figure 1:
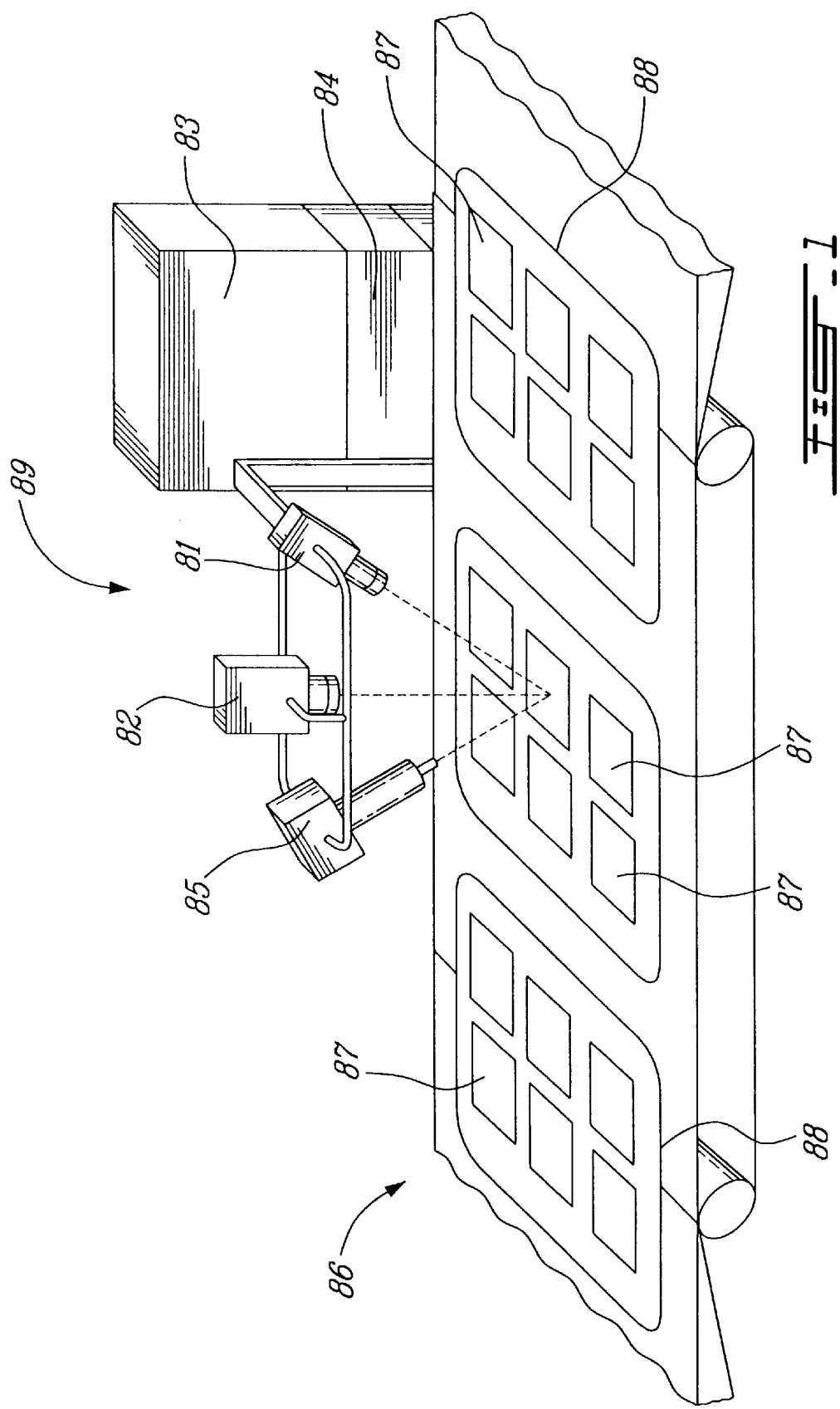
FIG. 1 depicts a schematic diagram of an implementation of one version of the preferred embodiment in a manufacturing process.

FIG. 1 depicts the overall system of the present invention as it might appear as part of a typical manufacturing process. The system of the present invention would typically make up part of a chip manufacturing facility, specifically the quality inspection portion of the operation. FIG. 1 depicts transportation mechanism 86 on which chips 87 with the BGAs are transported in industrial standard trays 88 through the scanning device 89. The system of the present invention includes one or more X-ray or light sources 81 illuminating the BGA chips 87 and one or more X-ray or light imaging devices 82. The imaging devices 82 in the preferred embodiment would output a digital signal of the images. These images are of the shadows cast by each individual solder ball upon illumination by the x-ray or light source 81.

The system includes a computer unit 83 with specifically designed software components for controlling the scanning process and analyzing the shadow images as well as specialized hardware components 84 to interface and link all the components of the system to the computer control unit. The system in the preferred embodiment also includes a labeling mechanism 85 to mark the chips according to their quality.

The inspection process consists of measuring height, position and shape of the solder balls based on an analysis of the shadows cast. Thus, the system from the information derived from this analysis determines the degree of colinearity and coplanarity of each BGA and whether they meet the predefined parameters. Here colinearity refers to the alignment of the ball positions into precise rows and columns. Coplanarity being the uniformity in height of the tops of each solder ball. Thus, coplanarity is the degree to which the top of each ball would form a point on the same plane. As noted above the BGA provides the means for connecting the circuitry of the IC chips to the outside world. Given the minute size of the chips and the solder balls of the BGA, a premium is placed on achieving precision in their placement and alignment. Otherwise the IC chip is worthless.

The transportation mechanism 86 moves the chips 87 through the inspection apparatus 89. The chips 87 are placed in industrial scanning trays 88 which carry the chips 87 along on the transport mechanism 86 through the inspection device 89. The transport mechanism consists of standard conveyor systems well know and extensively utilized in IC chip fabrication process. In inspection device 89 electromagnetic radiation sources 81 illuminate the BGA grid on each chip 87 in full or in part. Generally, the chips are placed on the trays 88 with the BGA arrays facing up, in what is know as the dead bug position, facing the illumination device or devices 81. Upon illumination the individual solder balls cast shadows. Imaging device 82 then transmits, in the preferred embodiment, digital images of the shadows to the computer unit which analyzes the shadows. Imaging devices and related apparatus for capturing an image and then transmitting it in digital form are well known in the art. In the preferred embodiment the imaging device is a high resolution CCD camera. However, any position sensitive detection device which provides the necessary resolution and is sensitive to the employed type of electromagnetic radiation can be used. From the analysis of the position, shape and length of each shadow, the system can quantify the colinearity and coplanarity of the solder ball array and then determine if it falls into acceptable tolerances. After making this determination, each chip is accordingly labeled and dealt with according to its quality at the appropriate stage of the manufacturing process.

If the field of view of the imaging device is smaller than the size of a chip, then the chip is scanned in sub-parts (e.g. x3, 4x4, 5x5 etc.). The source/detector imaging device assembly will move across the chip in a logical and predetermined order to sequentially scan all the sub-parts of the chip. In scanning the chip the changes in position of the source/detector imaging device assembly will be taken into account to obtain the positions necessary for assembling a complete image of the BGA on the chip thus assuring that the colinearity and coplanarity are correctly evaluated for the full BGA chip.

The invention will be better understood by following the detailed description of the two preferred embodiments.

First Preferred Embodiment: Implementation of Apparatus With X-ray Source

Figure 2:
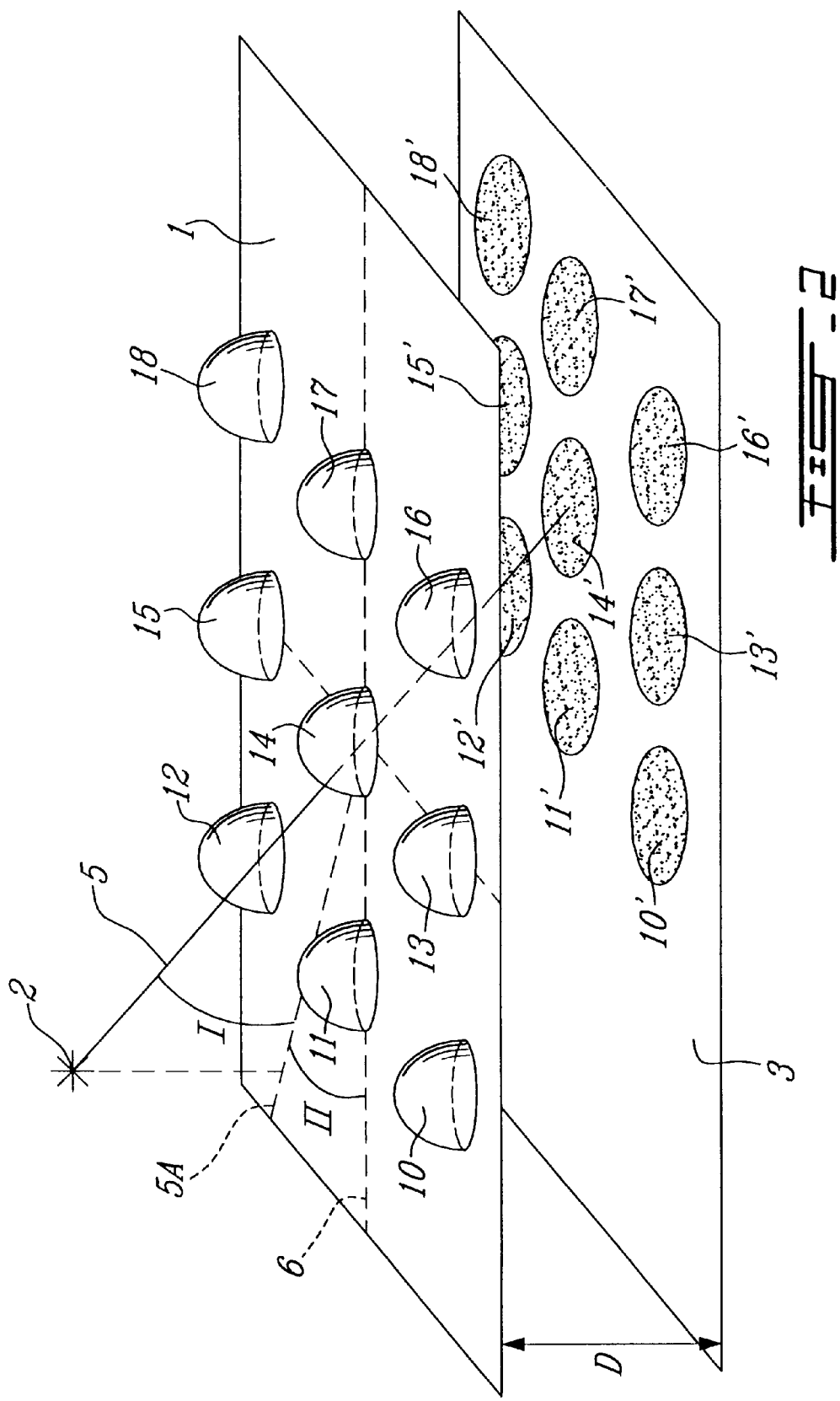
FIG. 2 depicts schematically a subsection of an illuminated BGA in a perspective view in one version of the preferred embodiment.

The preferred embodiment depicted in FIG. 2 uses electromagnetic radiation in the x-ray range. The x-ray source 2 and the x-ray detector 3 are on opposite sides of the inspection tray from each other. FIG. 2 depicts one subsection of the BGA in a perspective drawing. In FIG. 2 the solder balls, items 10 to 18, of the BGA, rest on a substrate 1 of the chip and the x-ray source 2 is positioned on one side, the side, in this case, on which the solder balls 10 to 18 are positioned with the imaging plane of the imaging device 3 located on the opposite side viewing the shadows 10' to 18' cast by the of solder balls 10 to 18 of the sub-grid array. Because of the penetrating nature of the X-rays an arrangement where the BGA chip would be flipped, i.e. the solder balls of the BGA chip would point downwards, is equally possible. The distance between the substrate I and the imaging device 3 in FIG. 2 is "D". The source of electromagnetic radiation, in this embodiment x-rays, projects the radiation for illumination down towards the substrate 1 so it strikes it at a predetermined angle of incidence "I". Additionally, a projection 5A of axis of illumination 5 of the x-rays onto the substrate 1 forms an angle "II" with the primary axis 6 of the orthogonal grid structure of the BGA on the substrate 1.

In the preferred embodiment, the predetermined angle "I", the illumination angle, at which the x-rays strike the substrate can be anywhere between 10 and 40 degrees. Angle "II", the orientation angle, in the preferred embodiment, can be between 5 and 40 degrees with respect to the orthogonal grid structure on the substrate of the BGA.

X-rays are generated at around energies of 60 keV in source 2 within a small focal spot of eight micrometers (8 μm) on the substrate. The energy level is chosen in such a way that the difference of the X-ray attenuation coefficients between the tin/lead mixture of the solder balls and the remaining less dense material is maximal. The X-ray shadow images 10' to 18' in FIG. 2 will thus show low intensities where the X-ray has largely crossed a solder ball and high intensities if the X-ray has missed or only partly crossed a solder ball.

The shadow images 10' to 18' of individual solder balls registered on the imaging surface of imaging device 3 are analyzed and among other things the positions and lengths of the shadow determined. Based on the information extracted, with respect to the shadows and the position of the X-ray source 2 with respect to the imaging plane of imaging device 3, one can approximate the height of the ball. It is easy to see that based on the information regarding the height and position of each of the balls the degree of colinearity and coplanarity of the BGA can be extracted. (Only the two angles are important for the version of the invention which uses the x-ray source. These are the illumination angle which can vary from 10 to 40 degrees and the orientation angle which can vary from 5 to 40 degrees. The absolute [i.e. x, y, z] position is not necessary.) Imaging device 3 can be any type of x-ray imaging devices which are well known to those skilled in the art and easily integrated into the invention. In the preferred embodiment a high resolution CCD camera is used as an x-ray imaging device. As entrance window of the CCD camera, an x-ray sensitive scintillator is used to convert the x-rays to visible light which is then registered by the CCD camera. However, any x-ray sensitive detector system providing the necessary position resolution can be used as an x-ray imaging device.

An advantage of this embodiment is that solder balls on the lower side of the chip can be inspected without the BGA directly facing the x-ray source.

Second Preferred Embodiment: Implementation of Apparatus With Light Source

Figure 3:
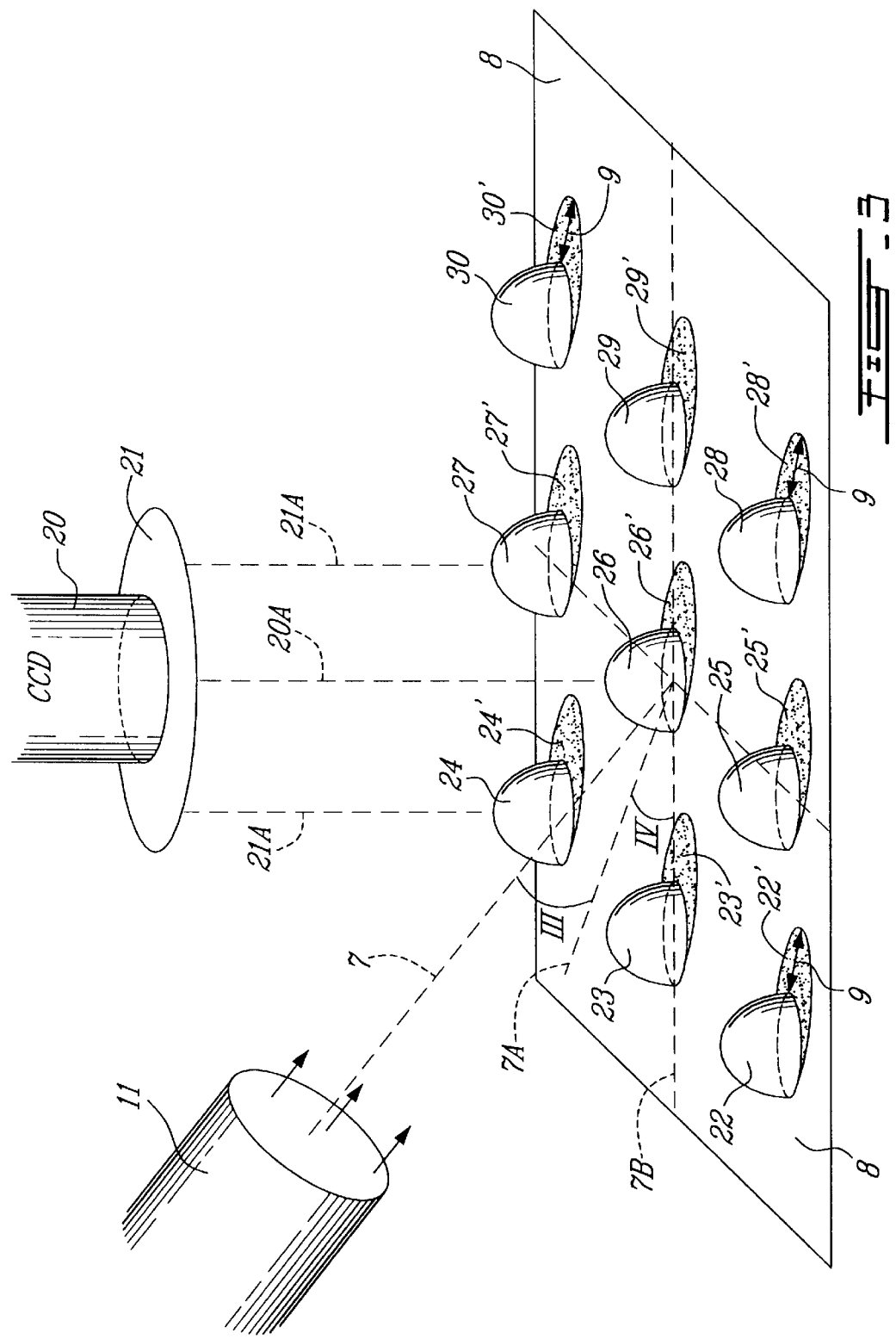
FIG. 3 depicts schematically a subsection of an illuminated BGA in another version of the preferred embodiment.

In this preferred embodiment, source and detector are on the same side of the inspection tray. FIG. 3 depicts one subsection of the BGA in a perspective drawing. The imaging device 20 views the solder balls from above the sub-grid array of solder balls. In this preferred embodiment, a parallel or point strobe light source 11 is used to illuminate the solder balls 22 to 30 of the BGA located on substrate 8. Shadows 22' to 30' result from illumination by strobe light source 11.

In this version the axis of illumination 7 of strobe light 11 forms an angle of incidence "III" with the substrate plane 8. In the preferred embodiment, angle III is between 10 and 40 degrees with respect to the substrate plane 8. Additionally, a projection 7A of axis 7 onto substrate 8 forms an angle "IV" with the primary axis 7B of the orthogonal grid structure of the BGA. In the preferred embodiment angle "IV" can vary anywhere from 5 and 40 degrees. Light source II generates a parallel beam of light and creates shadows opposite to the direction of light incidence. In a manner similar to the first preferred embodiment, the lengths 9 of the shadows items 22' to 30' are directly related to the height of solder balls 22 to 30. By analyzing the images taken with imaging device 20 the length of the shadow can be determined. Knowing the position of the light source 11 with respect to the substrate plane 8 and the length of the created shadow one can approximate the height of the ball. Imaging device 20, in the preferred embodiment, is a charged coupled imaging device (CCD), an apparatus well known by those skilled in the art. The optical axis 20A of imaging device 20 forms a perpendicular angle with substrate 8. This version of the preferred embodiment as well as the first which uses x-rays both have a much wider scope then the current methods used in the industry, in that they both allow a full 3-D inspection of the chip quality during the manufacturing process.

In addition, a second image can be taken by imaging device 20 directly from above with the ring strobe light 21. In the preferred embodiment the illuminating device 21 is a ring strobe light, which projects light parallel to the optical axis 20A of imaging device 20. Both the optical axis 20A of device 20 and the axis of illumination 21A or illumination source 21 form a perpendicular angle with the substrate 8. This second image facilitates the task of determining the contour of the shadow. This is accomplished in the preferred embodiment by comparing the image taken with strobe light 21 with the one taken with the strobe light 11. In this process residual reflections off the substrate can be identified and thereby a sharper definition of the shadow can be obtained.

Description of the Illumination Process Geometry

Figure 4:
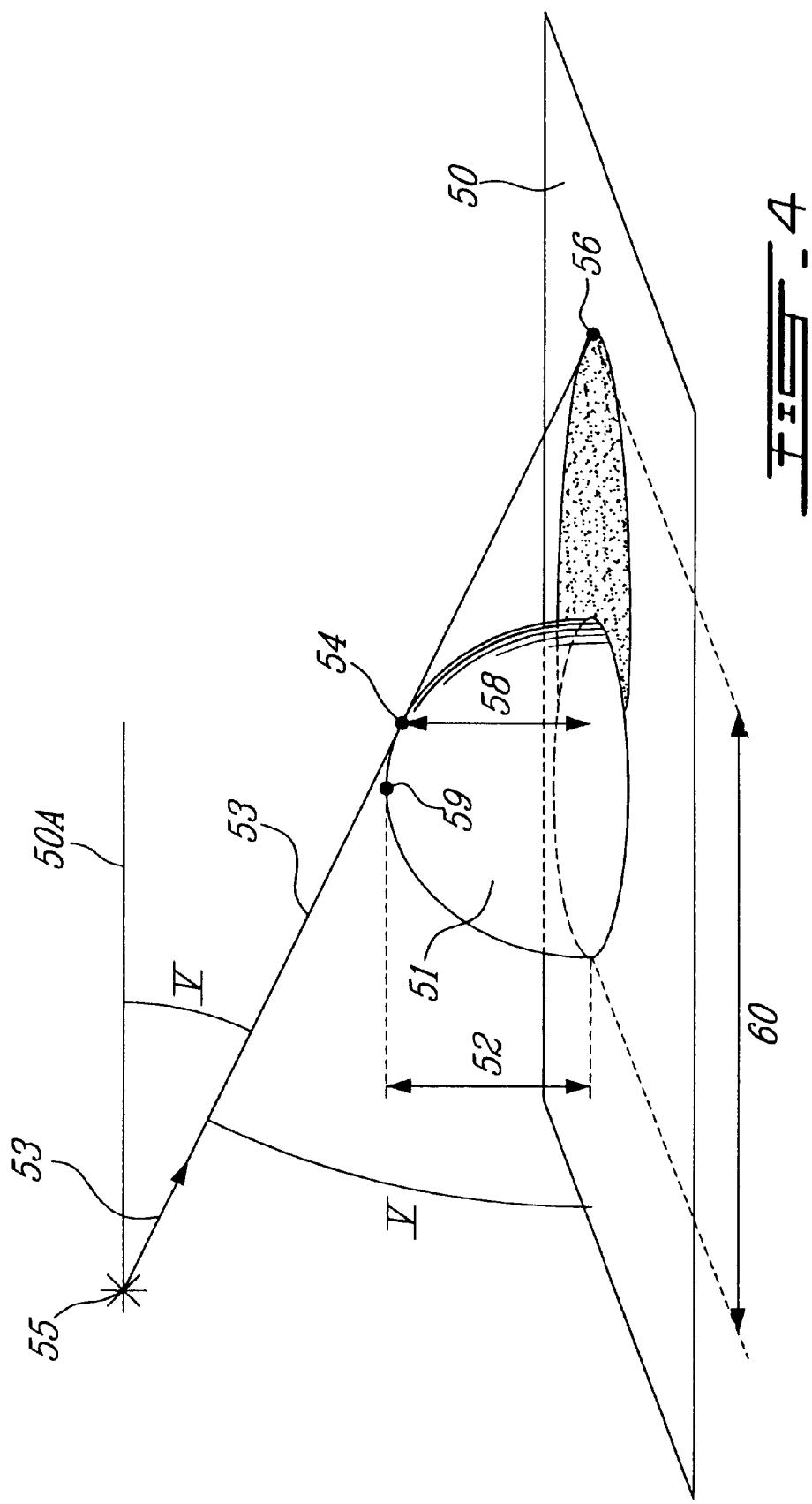
FIG. 4 schematically depicts the illumination of a single solder ball.

FIG. 4 demonstrates the illumination process of one individual ball. In FIG. 4: 50 is the substrate of the BGA and 51 is the illuminated ball having a height 52. The point 59 is the top of the ball and has the vertical distance 52 from the substrate 50. In both preferred embodiments, the ball 51 is illuminated by a source 55. The ray 53 from the source 55 touches the ball at the tangential point 54 and reaches the substrate 50 at the intersection point 56. The angle "V" is the angle at which the BGA is illuminated by the source 55. Line 50A is parallel to the plane of the substrate 50. The closer the tangential point 54 is to the top of the ball 59, the closer the value of the vertical distance 58 from the substrate to the tangent point is to the height of the ball 52. The vertical distance 58 is determined by trigonometry from the measured position of the intersection point 56 and the known illumination angle "V". As will be noted in more detail below, assuming a generally spherical shape for each solder ball, an approximation can be made correlating distance 58 with the actual height 52 of each solder ball. This provides sufficient information for a determination of coplanarity.

As noted above for the first preferred embodiment, the X-rays penetrate the substrate and the shadow image is formed on the imaging plane of the imaging device below the substrate. Additionally, for the second preferred embodiment, the light rays are cast on the substrate which also forms the focal plane of the imaging device positioned above the substrate. In both preferred embodiments, the obtained information from the shadow images are equivalent.

Height, Position and Ball Shape Measurements

The height, position and ball shape measurements are based on the contours of the shadows, which can be determined with standard edge detection techniques well known in the art.

As an example the vertical distance 58 (FIG. 4) is 98% of the true height 52 for an illumination angle of 11.5 degrees. With this illumination angle "V", the length of the shadow 60 of the ball 51 is five times the height 52 of the ball. Another illumination angle "V" of 14.5 degrees yields the vertical distance 58 to be 97% of the ball height 52 and yet another illumination angle "V" of 19.5 degrees yields the vertical distance 58 to be 94% of the ball height 52.

Since in any embodiment the illumination angle "V" is known, the measured shadow length can be corrected by the appropriate percentage. This yields a better estimate of the ball height. The calculation in the example above relies on the assumption that the solder ball is a semi-sphere.

The position of the ball is obtained from the shadow image by determining the center of gravity of the shadow.

The center of gravity of the shadow is calculated from the weighted mean of all the coordinates of those points lying within the shadow contour, where the weight for each coordinate is determined from the intensity value measured at that coordinate. The quality of the colinearity of the system is determined by examining how well the coordinates of the centers of gravity can be fitted into precise rows and columns.

Since the illumination angle "V" is known the expected shadow shapes can be precalculated and compared to the quality specifications defined for inspection of the solder balls. Thus actual analysis during the inspection process would involve comparing the precalculated shadow shape with the actual shadow shape imaged during the inspection.

As noted the calculation in the example above assumes a semi-spherical shape for each solder ball above the substrate plane. However, under certain circumstances the solder ball could have a different shape. For example there exist BGA chip designs, where the shape of the solder ball above the substrate corresponds to 70% of a full solder ball sphere. In such a situation the new geometrical model of the solder ball can easily be incorporated into the analysis procedure of the system. The same statement also holds for the case where instead of solder balls solder columns are examined and the spherical model is replaced by a cylindrical model. No matter what shape is assumed the invention described herein would allow for the incorporation of such different shapes and still function as envisioned.

Adjustment of the Illumination Angle

A smaller illumination angle (FIG. 4—angle V, FIG. 2—angle I, FIG. 3—angle III) requires a smaller correction between the derived vertical distance 58 and the ball height 52. In other words, as the tangential point 54 approaches the top of the ball 59 the more closely its distance from the substrate approximates the height of the solder ball. In this way, the height of a solder ball as well as irregularities and defects of the ball shape close to its top 59 are more precisely examined. Additionally, a smaller illumination angle creates longer shadows, and hence better sensitivity for the height and shape measurements. A given variation of the height gives a larger change of the shadow length.

On the other hand, a smaller illumination angle results in images with lower contrast between the shadow and non-shadow areas, and can lead to overlapping of the imaged objects. Thus, optimal illumination angle is selected based on the preceding criteria.

A Variation to the Preferred Embodiment With Multiple Sources

One variation of the preferred embodiment uses a multiple of X-ray or light sources (e.g. two or four, etc.). They illuminate the BGA chip at the same angle of incidence (FIG. 2 angle I, FIG. 3 angle III and FIG. 4 angle "V") but from different directions. We have defined herein equidistant angle to mean that with a given set of items each of which is on the circumference of the circle they are all at equidistance from each other as you move along the circumference of the circle. FIG. 5 depicts an arrangement with four light sources 41', 41", 41'" and 41"". The sources are positioned at equidistant angles (360/2=180 degrees; 360/4=90 degrees) around the imaging area. FIG. 5B provides an overhead view of the positioning of the light sources showing how the equidistant angles appear from above. Thus, as depicted in FIG. 5B the equidistant angle between the four illumination sources is 90 degrees. FIG. 5A depicts the shadows 31', 31", 31'" and 31"" formed by the solder balls illuminated by the four sources of electromagnetic radiation. If only two sources are used then the light sources would be at the equidistant angle of 180 degrees from each other. For instance 41' and 41'" depict how two sources would be used instead of four. Using a two source arrangement you would only see two shadows 31' and 31'". The multiple shadows, created by the multiple sources are captured either in one or in two separate images.

Instead of using four or two separate sources the same images can be obtained by rotating the inspection tray by the above mentioned equidistant angles under the illumination of one source. Alternatively, instead of rotating the inspection tray a single source of illumination could be rotated to the two or four different positions located at equidistant angles from each other and achieve the same effect.

FIG. 5 depicts one subsection of the BGA in perspective drawing. Imaging device 49 is positioned over the substrate 19. The substrate 19 which has positioned thereon the solder balls 31 to 39 of the BGA. The solder balls of the subsection of the BGA, cast four shadows upon illumination. FIG. 5A provides an example of the four shadows 31', 31", 31'", 31"" generated from ball 31 by the four sources 41', 41", 41'", 41"". Both FIGS. 5 and 5A depict the shadows of solder ball 31. Although not numbered each of the other solder balls on FIG. 5 likewise produce four shadows.

The angles of incidence "VII" at which the light sources 41', 41", 41'", 41"" illuminate the BGA are all equal and chosen to allow for the longest shadows compatible with the rectangular grid-structure of the BGA. Combining the two opposite shadows, e.g. 31' and 31'" an average measurement of the height of the ball is obtained. Referring to FIG. 5A this is accomplished by measuring the distance 44 between the two points 43 and 43', instead of measuring the two shadows separately. This approach reduces the measurement error on the ball height. Combining this average height with the evaluation of the average obtained from the perpendicular shadow pair gives another average taking into account the measurements of all four shadows and thus further reduces the chance for errors. Although the height of a ball can be determined from one shadow only, this method gives redundant measurements and provides the BGA inspection device with more precise and robust results.

Another Variation for Determining Warpage

Additionally, with the x-ray version in the multiple illumination source version modified tomographic methods can be used to obtain full 3-dimensional information of the solder ball shape and position. The modified tomographic method is adapted from the classic tomographic methods and would employ the setup as depicted in FIG. 5. The setup differs from the classic tomography method in that the angle of incidence VII is greater than 0 degrees. The modified tomographic method implies the back-projection of each single registered shadow towards the location of the source which has produced the shadow. The intersection of these back-projections will trace the 3-dimensional contour line along which the ball is attached to the substrate. This 3-dimensional information is determined with respect to the planar imaging surface of the imaging device. Thus, the 3-dimensional information obtained can be used to extract the coplanarity (warpage) of the substrate at the base of each solder ball.

The light version of the multiple illumination source variation does not have a similar capability. This is due to the fact that the image is formed by reflection off the substrate and the 3-dimensional information obtained with light is with respect to the substrate. And thus the warpage of the substrate itself cannot be determined using multiple light sources.

A Variation to the Second Preferred Embodiment: Absolute Three-Dimensional Imaging With Multiple Light Imaging Devices In the case of the illumination of a BGA with one light source three-dimensional ball information can be obtained by using multiple imaging devices. In this variation as depicted in FIG. 6 two detection devices 70 and 71 can be used for obtaining additional images with which to determine substrate coplanarity and warpage. The optical axis 71A of the imaging device 71 forms a perpendicular angle "IX" with the substrate. Imaging device 70 is positioned such that its optical axis 70A forms an angle of incidence VIII with substrate 68. In the preferred embodiment, angle VIII is approximately 45 degrees. Each of the imaging devices 70 and 71 captures an image of the section of the BGA with illumination provided from above with the ring strobe light 72. The axis of illumination of ring light 72 is parallel to optical axis 71A and thus perpendicular to the substrate 68.

The first image from imaging device 71 directly from above is analyzed and the 2-dimensional positions of the balls within the two planar dimensions of substrate 68 are determined. This information can be used to verify the balls' correct X-Y positions on the substrate within the orthogonal grid array. The balls' perimeters are extracted by using edge detection techniques. The second image from imaging device 70 viewing the BGA from angle VIII is analyzed and the positions of the balls' visible half perimeters are determined. The opposite half perimeters are occluded by the balls.

3-dimensional information on the coplanarity (warpage) of the substrate at the base of each solder ball can be obtained by applying backprojection techniques similar to the ones discussed above. The intersection of the backprojection of the first image (i.e. the projection of the balls' perimeter along the axis 71A) with the backprojection of the second image (i.e. the projection of the balls half perimeter along the axis 70A) the 3-D dimensional position of the substrate in the neighborhood of one side of the full perimeter of the ball.

In order to obtain the complete three-dimensional measurements of the substrate warpage close to the ball perimeter, a third imaging device 75 positioned opposite imaging device 70 can be used. The optical axis 75A of imaging device 75 forms the same angle of incidence "VIII" with the substrate 68. As noted in the preferred embodiment, this is 45 degrees. Thus the second half of the perimeter of the solder ball is imaged. Backprojection of this half perimeter and intersection with the backprojection of the full perimeter provides the complete 3-dimensional information.

Another alternative would involve positing a strobe light at 75 instead of an imaging device. A strobe light placed in a position at 75, produces a ball shadow visible to the imaging devices 70 and 71. The balls' shadows are imaged with both imaging devices 70 and 71. By matching the first and the second image, using again backprojection techniques, the 3-dimensional contour lines of the balls' shadows are determined.

Based on the three-dimensional information of the balls' perimeters or shadows, the coplanarity (warpage) of the substrate in the region of the ball shadow can be determined.

The Functional Block Diagram of the Inspection Apparatus

The block diagram in FIG. 7 provides a functional overview of the complete inspection process. As discussed above several implementations of the apparatus are possible: a.) X-ray versus light for illumination; b.) choice of inspection criteria (e.g. colinearity, coplanarity, ball shape analysis); c.) single versus multiple sources; d.) 2 dimensional versus 3 dimensional (multiple sources only) imaging; e.) 3 dimensional reconstruction of ball perimeter and shadow contour with one light source and multiple imaging devices. Optional features are included in the diagram of FIG. 7 as dashed boxes or lines.

The main sections of the apparatus of the invention depicted in FIG. 1 appear again in FIG. 7. These include some of the components of the transportation unit 86 which includes the conveyor belt 105 and the inspection tray 102. The scanning unit 89 including the source of illumination 108 and the imaging device or devices 109 and 109'. In general a multiple of illumination sources 108 or a multiple of imaging devices 109 can be included in the scanning unit 89. The interface 84 together with its major components is located between lines A and B. Finally, the computer unit 83 and its major components are located below line B. The functional relationships of all the component parts are represented in FIG. 7 by the solid lines which joint each component part. The direction of signals passing between the functionally related component parts being indicated by the arrow head on each solid line. The path of illumination between the illumination source 108 and the chip as well as the imaging path between the chip 101 under inspection are represented by dashed lines with an arrow head indicating the direction of illumination and imaging. Finally, FIG. 7 shows which functional parts, in the preferred embodiment, are implemented in the computer unit 83 and which are implemented in the interface hardware 84.

The IC chip 101 with the BGA 101A to be inspected is positioned on an inspection tray 102. The main control logic unit 103 is connected to a set of other specific control units. These control units are: a) the motion control unit 104, which controls the movement of a conveyor belt 105 on which the inspection tray 102 is located, b) the source control unit 106, which strobes the X-ray or light sources 108 and c) the imaging device control unit 107, which directs the readout cycle of the imaging devices 109.

First, the main control logic 103 signals the motion control unit 104 to position the tray 102 with the subject chip 101 which has the BGA 101A to be inspected. Then main control logic 103 signals the source control unit 106 to activate the illumination source 108, and simultaneously the imaging device control unit 107 to record an image. Image control unit 107 accordingly sends the appropriate signal to the imaging device 109 and 109' if necessary. Upon obtaining the image the imaging device 109 sends the image obtained to image buffer 110. If imaging device 109' is activated it sends its image to image buffer 123.

When only one source of illumination or only one imaging device is used for the purpose of obtaining one 2-dimensional image the image obtained is passed for processing to the image analysis engine 112 through image buffer 110. If more than one source of illumination 108 is used for illuminating the inspected BGA chip 101, the reconstructor 111 can offer full 3-dimensional image reconstruction. The reconstructor transforms several 2-dimensional projection images into one 3-dimensional image by applying modified tomographic methods. Hence, a 3-dimensional image can be passed for processing to the image analysis engine 112. The input to the analysis engine 112 consists of an image. The image analysis engine 112 can be implemented for two- or three-dimensional images.

The image analysis engine 112 includes the following components: 1.) The ball position finder 113, which calculates from the input image the ball positions. 2.) The colinearity extractor 114, which calculates from the ball positions the colinearity. 3.) The ball height extractor 115, which calculates from the input image and the ball position the ball heights. 4.) The coplanarity extractor 116, which calculates from the ball heights the coplanarity. 5.) The ball shape comparator 117, which compares the expected ball shape to the ball shape from the input image and calculates the ball shape coefficients which quantify the difference of the expected and the actually measured shapes. 6.) The ball base position finder 118, which calculates from the 3-dimensional input image and the ball positions the ball base positions. A ball base is the intersection between a solder ball and the substrate plane. The ball base position is the center of gravity of the ball base. The substrate warpage extractor 119, which calculates from the ball base positions the substrate warpage.

The image analyzing engine 112 thus determines the ball heights, colinearity, coplanarity, ball shape coefficients, substrate coplanarity (warpage). It then passes these results on to the inspection criteria decision logic unit 120, which compares these values so obtained to the predetermined specifications. The decision logic unit 120 after an analysis makes a determination as to quality of the BGA on the chip and then passes this determination onto the main control logic 103. The main control logic activates the chip quality labeling mechanism 121 which accordingly labels the chip with the appropriate information.

Although the 2-dimensional imaging process is adequate for the purposes used, the system as depicted provides options of obtaining three dimensional images for analysis. One option is the application of the 3D reconstructor 111 in the case of multiple X-ray sources 108 and one imaging device 109. Another option includes the 3D reconstructor 124 for the case of multiple imaging devices 109 and one light source for illumination 108. This absolute 3-dimensional light imaging option 122 comprises additional image buffers 123 (one per imaging device 109), a 3D reconstructor 124, a ball perimeter position finder 125 and substrate warpage extractor 126. The 3D reconstructor 124 transforms several 2-dimensional projection images of contour lines into one 3-dimensional contour line image. The contour in this case being the solder balls perimeter or 3D shadow contour. The ball perimeter position finder 125 finds the 3-dimensional positions of the reconstructed perimeters. The substrate warpage extractor 126 calculates from the 3-dimensional perimeter positions the substrate warpage.

A Multiple of Measurement Setups

The scanning process is easily implemented as a parallel process. Multiple measurements can be obtained simultaneously with multiple scanning units which would inspect different sub-regions of the BGA at the same time. The processing of the different data streams acquired in a concurrent mode is identical to a sequential processing operation. This will improve the throughput efficiency of the inspection apparatus.

CONCLUSION

The invention described herein refers to a solder ball grid array in describing the invention; however, the invention can be extended to in a straight forward manner to any structure consisting an assembly of regularly formed objects, e.g. column grid arrays where the solder balls are replaced by solder columns or some similar regular array of minute objects.

While the invention has been particularly shown and described with reference to a preferred embodiment thereof, it will be understood by those skilled in the art that various changes in form and detail may be made to it without departing from the spirit and scope of the invention.

We claim:

1. A system for inspecting a ball grid array on an integrated circuit for verifying if said array conforms to specific position parameters, the system comprising:
    a source of electromagnetic radiation projected at a predetermined angle onto a substrate of the integrated circuit on which substrate surface is said array;
    an imaging device to obtain an image of shadows cast by balls of the ball grid array; and
    an image analysis engine to analyze said image to obtain contour data of the shadows cast by the balls.

2. The system of claim 1 wherein the system comprises further an inspection criteria decision logic unit to analyze said contour data to obtain ball position or dimensional data to determine if a position or dimension of said balls meet certain predefined parameters whereby the system can verify if the balls meet these predefined parameters.

3. The system of claim 1 wherein the electromagnetic radiation projected onto the substrate, on which said array is located, to create the shadows is selected from the group consisting of x-rays and light.

4. The system of claim 1 wherein the predetermined angle is the angle at which an axis of illumination of the electromagnetic source strikes the substrate on which the ball grid array is located and that angle is selected from any angle between 10 to 40 degrees; and wherein the balls of the ball grid array form an orthogonal grid array structure with a primary axis on the substrate of the integrated circuit and an angle on the substrate which a projection onto the substrate of the axis of illumination makes with the primary axis of the orthogonal grid structure can be selected from any angle between 5 to 40 degrees.

5. The system of claim 1 further comprising a second source of electromagnetic radiation with an axis of illumination parallel to an optical axis of the imaging device, the axis of both being perpendicular to the substrate, whereby the system can compare images obtained by the imaging device with radiation generated by the source of electromagnetic radiation set at the predetermined angle with images obtained by the second source of electromagnetic radiation and thereby obtain a sharper definition of the shadows cast by illumination with the source set at the predetermined angle.

6. The system of claim 1 wherein the source of electromagnetic radiation provides illumination of the integrated circuit at the predetermined angle to the substrate from at least two different directions so that at least two different shadows of each ball of the array are provided for analysis.

7. The system of claim 6 wherein two separate images are taken by the imaging device one from each of the at least two different directions.

8. The system of claim 6 wherein the imaging device takes one image with illumination provided from the at least two different directions at the same time.

9. The system of claim 6 wherein the at least two different directions are at equidistant angles from each other.

10. The system of claim 6 wherein illumination of the integrated circuit at the predetermined angle to the substrate from at the at least two different directions further comprises illuminating the array from four different directions at the predetermined angle and wherein the four different directions are positioned at equidistant angles from each other.

11. The system of claim 6 wherein the illumination of the array from at least two different directions at the same predetermined angle provides data to construct a three dimensional image of the of the balls of the array for analysis.

12. The system of claim 6 wherein the system uses the images obtained to produce a three dimensional image for analysis.

13. The system of claim 1 wherein the imaging device comprises at least two imaging devices to image the ball grid array from at least two different directions whereby the data so obtained can be used by the system to produce three dimensional images of the array.

14. The system of claim 2 wherein the predefined parameters are selected from a group of: coplanarity, colinearity, ball shape analysis, and warpage.

15. A method for verifying that an array of minute objects on a workpiece conform to specific parameters, said method comprising:

projecting electromagnetic radiation at a predetermined angle onto a substrate surface of the workpiece on which substrate surface are positioned an array of minute objects;

imaging the shadows cast by the minute objects as a result of being illuminated by the electromagnetic radiation;

analyzing the images so obtained to determine if the array of minute objects meet certain predefined parameters.

16. The method of claim 15 wherein projecting electromagnetic radiation at a predetermined angle onto the substrate surface of the workpiece comprises projecting it so that an axis of illumination of the radiation so projected intersects the substrate surface at an angle selected from any angle between 10 and 40 degrees.

17. The method of claim 15 wherein projecting electromagnetic radiation further comprises projecting it so that a projection of a path of the axis of illumination onto the substrate surface forms, with a primary axis of an orthogonal grid structure of the ball grid array on the substrate, an angle selected from any angle between 5 to 40 degrees.

18. The method of claim 15 wherein projecting electromagnetic radiation at a predetermined angle onto the substrate surface of the workpiece further comprises projecting such radiation from at least two different directions but at the same predetermined angle so that at least two shadows are cast by each object of the grid array.

19. The method of claim 17 wherein the step of projecting radiation further comprises projecting radiation from the at least two different directions at equidistant angles from each other.

20. The method of claim 18 comprising the additional step of creating a three dimensional representation of the minute objects located on the substrate from the images obtained.

21. The method of claim 15 wherein the step of imaging the substrate with the minute objects thereon further comprises imaging it from at least two different directions so that from the data obtained three dimensional representations of the minute objects on the substrate can be created.

22. The method of claim 15 where in the step of projecting radiation comprises generating radiation selected form the group of x-rays and light.

23. The method of claim 15 wherein the predefined parameters are selected from a group of: coplanarity, colinearity, ball shape analysis, and warpage.

24. A system for verifying that an array of minute objects on a workpiece conform to specific parameters, the system comprising:

a source of electromagnetic radiation projected at a predetermined angle onto a substrate of the work piece on which substrate surface are an array of minute objects, an imaging device to image the shadows cast by the minute objects, an image analysis engine to analyze the shadows cast to determine if the minute objects and substrate meet certain predefined parameters.

25. The system of claim 24 wherein the predefined parameters are selected from a group of: coplanarity, colinearity, ball shape analysis, and warpage.

* * * * *